US009827305B2

(12) United States Patent
Qiao et al.

(10) Patent No.: US 9,827,305 B2
(45) Date of Patent: Nov. 28, 2017

(54) POULTRY VIRUS VACCINES THAT ARE LIQUID STABLE

(71) Applicant: Intervet Inc., Madison, NJ (US)

(72) Inventors: Zhisong Qiao, Omaha, NE (US); Stephanie Cook, Omaha, NE (US); Kevin O'Connell, Omaha, NE (US); Ian Tarpey, St. Ives (GB)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/119,014

(22) PCT Filed: Feb. 16, 2015

(86) PCT No.: PCT/EP2015/053188
§ 371 (c)(1),
(2) Date: Aug. 15, 2016

(87) PCT Pub. No.: WO2015/121463
PCT Pub. Date: Aug. 20, 2015

(65) Prior Publication Data
US 2016/0346381 A1    Dec. 1, 2016

Related U.S. Application Data

(60) Provisional application No. 61/940,627, filed on Feb. 17, 2014.

(51) Int. Cl.
| A61K 39/215 | (2006.01) |
| A61K 47/26 | (2006.01) |
| A61K 47/18 | (2017.01) |
| C12N 7/00 | (2006.01) |
| A61K 39/12 | (2006.01) |
| A61K 9/00 | (2006.01) |
| A61K 39/00 | (2006.01) |

(52) U.S. Cl.
CPC .......... *A61K 39/215* (2013.01); *A61K 9/0019* (2013.01); *A61K 39/12* (2013.01); *A61K 47/183* (2013.01); *A61K 47/26* (2013.01); *C12N 7/00* (2013.01); *A61K 2039/5252* (2013.01); *A61K 2039/5254* (2013.01); *A61K 2039/5256* (2013.01); *A61K 2039/54* (2013.01); *A61K 2039/552* (2013.01); *A61K 2039/70* (2013.01); *C12N 2770/20021* (2013.01); *C12N 2770/20034* (2013.01)

(58) Field of Classification Search
None
See application file for complete search history.

(56) References Cited

U.S. PATENT DOCUMENTS

| 3,155,589 A | 11/1964 | Slater et al. |
| 3,526,696 A | 9/1970 | Gale |
| 4,337,242 A | 6/1982 | Markus et al. |
| 4,451,569 A | 5/1984 | Kobayashi et al. |
| 5,443,959 A | 8/1995 | Kikuchi et al. |
| 5,565,318 A | 10/1996 | Walker et al. |
| 5,593,824 A | 1/1997 | Tremi et al. |
| 5,763,409 A | 6/1998 | Bayol et al. |
| 5,932,223 A | 8/1999 | Burke et al. |
| 6,039,958 A | 3/2000 | Koyama et al. |
| 6,231,860 B1 | 5/2001 | Fanget et al. |
| 6,331,303 B1 | 12/2001 | Briggs et al. |
| 6,931,888 B2 | 8/2005 | Shekunov et al. |
| 7,073,349 B2 | 7/2006 | Shekunov et al. |
| 7,351,416 B2 | 4/2008 | Briggs et al. |
| 7,959,929 B2 | 6/2011 | Crawford et al. |
| 8,192,747 B2 | 6/2012 | Vande Velde |
| 8,980,610 B2 | 3/2015 | Selvitelli et al. |
| 9,314,519 B2 | 4/2016 | Qiao et al. |
| 9,393,298 B2 | 7/2016 | Buchanan et al. |
| 2004/0038878 A1 | 2/2004 | Tanikawa et al. |
| 2004/0154317 A1 | 8/2004 | Shekunov et al. |
| 2005/0178020 A1 | 8/2005 | Shekunov et al. |
| 2007/0148765 A1 | 6/2007 | Evans et al. |
| 2007/0161085 A1 | 7/2007 | Trager et al. |
| 2007/0190163 A1 | 8/2007 | Malaknov et al. |
| 2007/0259348 A1 | 11/2007 | Phadke et al. |
| 2008/0166784 A1* | 7/2008 | Chen .................. A61K 9/0019 |
| | | 435/235.1 |
| 2008/0248551 A1 | 10/2008 | Stinchocomb et al. |
| 2009/0010955 A1 | 1/2009 | Kapil et al. |
| 2009/0274734 A1 | 11/2009 | Daamen et al. |
| 2010/0015180 A1 | 1/2010 | Francon et al. |
| 2010/0124557 A1 | 5/2010 | Oberreither et al. |
| 2010/0196420 A1 | 8/2010 | Kapil |
| 2010/0297231 A1 | 11/2010 | Vehring et al. |
| 2011/0081380 A1 | 4/2011 | Francon et al. |

(Continued)

FOREIGN PATENT DOCUMENTS

| EP | 0028563 A1 | 5/1981 |
| EP | 0650734 | 10/1993 |

(Continued)

OTHER PUBLICATIONS

Burke et al. (Critical Reviews in Therapeutic Drug Carrier Systems. 1999; 16 (1): 1-83).*
Medi (European Pharmaceutical Review. 2014; 19 (1): 16-20).*
Auser et al. (Human Vaccines. 2007; 3 (3): 68-77).*
Morefield (The AAPS Journal. Jun. 2011; 13 (2): 191-200).*
Cavanagh, et al., Coronavirus avian infectious bronchitis virus, Veterinary Research, 2007, pp. 281-297.
International Search report for PCT/EP2015/053188 dated Aug. 12, 2015, 16 pages.
Morefield, Gary, A Rational, Systematic Approach for the Development of Vaccine Formulations, The AAPS Journal, 2011, pp. 191-200, 13-2.
Schlehuber, et al., Towards Ambient Temperature-stable vaccines: The identification of thermally stabilizing liquid formulations for measles virus using an innovative high-throughput infectivity assay, Vaccine, 2011, pp. 5031-5039, 29.

(Continued)

Primary Examiner — Shanon A Foley

(57) ABSTRACT

The present invention is drawn to liquid stable poultry vaccines that comprise avian virus. The invention is also drawn to the manufacture of such vaccines methods of vaccinating animal subjects with these vaccines.

23 Claims, No Drawings

(56) References Cited

U.S. PATENT DOCUMENTS

| | | | |
|---|---|---|---|
| 2012/0213810 A1 | 8/2012 | Burgard et al. | |
| 2014/0056942 A1 | 2/2014 | Qiao et al. | |
| 2016/0346381 A1* | 12/2016 | Qiao | A61K 39/12 |

FOREIGN PATENT DOCUMENTS

| | | |
|---|---|---|
| EP | 1123710 A1 | 8/2001 |
| GB | 1575155 | 9/1980 |
| JP | 61053227 | 3/1986 |
| WO | 8906973 A1 | 8/1989 |
| WO | 03087327 A2 | 10/2003 |
| WO | 2004017990 A1 | 3/2004 |
| WO | 2007035455 A2 | 3/2007 |
| WO | 2007056847 A1 | 5/2007 |
| WO | 2008107908 A1 | 9/2008 |
| WO | 2008143782 A1 | 11/2008 |
| WO | 2009109550 | 9/2009 |
| WO | 2010125084 A1 | 11/2010 |
| WO | 2010125087 A1 | 11/2010 |
| WO | 2009092703 A1 | 6/2011 |
| WO | 2011072218 | 6/2011 |
| WO | 2014009328 A1 | 1/2014 |
| WO | 2014029702 A1 | 2/2014 |
| WO | 2014140239 A1 | 9/2014 |
| WO | 2015044337 A2 | 4/2015 |
| WO | 2015121463 A2 | 8/2015 |
| WO | 2015124594 A1 | 8/2015 |

OTHER PUBLICATIONS

Anonymous, "Nobivac DHPPi" —XP002714517,Retrieved from the Internet: URl:http://www.msd-animal-health.co.nz/binaries/Nobivac DHPPi website label Feb. 12 t cm51-37104.pdf - - - —[retrieved on Oct. 10, 2013] the whole document.

Arakawa, et al., Biotechnology applications of amino acids in protein purification and formulations, Amino Acids, 2007, 587-605, 33.

Ausar, et al., Analysis of the Thermal and pH Stability of Human Respiratory Syncytial Virus, Molecular Pharmaceutics, 2005, 491-499, 2-6.

Brandau, et al., Thermal Stability of Vaccines, Journal of Pharmaceutical Sciences, 2003, 218-231, 92-2.

Chen, et al., Opportunities and challenges of developing thermostable vaccines, Expert Reviews, 2009, 547-557, 8-5.

Chokephaibulkit et al., Challenges for the formulation of a universal vaccine against dengue, Experimental Biology and Medicine, 2013, pp. 566-578, 238.

Crawford, et al., Transmission of Equine Influenca Virus to Dogs, Science, 2005, 482-485, 310, US.

Derwent; English Abstract of JP61053227; Title: Mixed live vaccine for Japanese encephalitis and swine parvovirus infection; Sasaki; Mar. 17, 1986.

Ellingson, et al., Vaccine efficacy of porcine reproductive and respiratory Syndrome Virus Chimeras, Vaccine, 2010, pp. 2679-2686, 28.

Intervet UK Ltd., The UK's Favourite Small Animal Vaccines; the Nobivac Range, Nobivac, The Future of Vaccination, 2006, XP002714516; 1-48, 1.

Kamerzell, et al., Protein-excipient interactions: Mechanisms and biophysical characterization applied to protein formulation development, Advanced Drug Delivery Reviews, 2011, 1118-1159, 63.

Lee, et al., Dog-bites and local infection with *Pasteurella septica*, British Medical Journal, 1960, pp. 169-171, 1.5167.

Mochizuki, Masami, Growth characteristics of canine pathogenic viruses in MDCK cells cultured in RPMI 1640 medium without animal protein, Vaccine, 2006, pp. 1744-1748, 24.

Papatsiros, Porcine Respiratory and Reproduction Syndrome Virus Vaccinology: A Review for Commercial Vaccines, American Journal of Animal and Veterinary Sciens, 2012, pp. 149-158, 7-4.

Patel, et al., Stability Consideration for Biopharmaceuticals, Part 1, BioProcess Technical, 2011, 1-10.

Saif, Linda, Bovine Respiratory Coronavirus, Veterinary Clinics of North America: Food Animal Practice, 2010, pp. 349-364, 26(2), US.

Schering-Plough Animal Health Ltd., Nobivac DHPPi; Combined Live Attenuated Freeze-Dried Canine Distemper Virus, Adenovirus Type 2, Parvovirus and Parainfluenza Virus Vaccine, Restricted Veterinary Medicine, 2013, XP002714517; 1-2, 1.

Taguchi, et al., Antibody titers for canine parvovirus type-2, canine distemper virus, and canine adenovirus type-1 in adult household dogs, Canine Veterinary Journal, 2011, 983-986, 52.

Tompkins, et al., Recombinant parainfluenza virus 5 (PIV5) expressing the influenza A virus, Virology, 2007, pp. 139-150, 16(1).

* cited by examiner

POULTRY VIRUS VACCINES THAT ARE LIQUID STABLE

CROSS-REFERENCE TO RELATED APPLICATIONS

This application is a national stage entry under 35 U.S.C. §371 of PCT/EP2015/053188 filed on Feb. 16, 2015, which claims priority to U.S. Provisional Application 61/940,627. The content of PCT/EP2015/053188 is hereby incorporated by reference in its entirety.

FIELD OF THE INVENTION

The present invention pertains to liquid stable poultry vaccines that comprise a live avian virus. The invention also pertains to the manufacture of such vaccines and methods of vaccinating animal subjects.

BACKGROUND

There are a significant number of viruses that can infect poultry. Such viruses include infectious bronchitis virus (IBV), infectious bursal disease virus (IBDV), Newcastle disease virus (NDV), Infectious Laryngotracheitis (ILTV), Mareks disease virus (MDV), Herpesvirus of Turkeys (HVT) which is also known as MDV3, and avian metapneumoviruses (aMPV). There also are a number of bacteria that can infect poultry, including *Pasteurella multocida, Salmonella* ssp., *Escherichia coli, Mycoplasma* ssp., *Avibacterium paragallinararum, Erysipelas* ssp., *Campylobacter* ssp., *Vibrio* ssp., and *Clostridium perfringens*. Parasites, such as *Eimeria*, also can infect poultry.

It is now widely accepted that the best way of preventing disease due to bacterial, parasital, or virus infections in poultry is to vaccinate them against these organisms. Moreover, multivalent live attenuated virus or bacterial vaccines can be safely administered that limit the number of vaccine injections required. Accordingly, there are many commercially available multivalent live virus vaccines that protect against multiple pathogens. However, heretofore, live attenuated avian viruses have been unstable when stored in liquid solutions. Therefore, most live attenuated avian virus vaccines are lyophilized, i.e., freeze-dried or frozen, prior to their long-term storage. The live attenuated avian virus is commonly mixed as a suspension in water with a protective agent, frozen, and then dehydrated by sublimation and secondary drying during the lyophilization process. The low temperatures of freezing and drying by sublimation, together with the low surface to volume ratios involved, can require long drying periods and thereby, significantly increase manufacturing time and costs.

In addition, there are inherent inconsistencies in large commercial drying processes due to: the inability to adjust the shelf temperature across the entire product load, variable freezing rates across the dryer, edge effects, and radiant energy effects. Increasing the drying temperature to reduce drying times is often not an option since the drying temperature has to remain significantly below the glass-transition temperature of the protective protein matrix. Moreover, the long inconsistent drying times and/or high drying temperatures often lead to structural damage to the live attenuated viruses, along with a significant loss of their biologic activity.

Consequently, in order to account for the inherent loss in efficacy, lyophilized poultry vaccines that comprise live attenuated viruses are stored with augmented titers. However, such increased titers can lead to significant adverse events should the lyophilization process actually lead to less loss of activity than anticipated. Therefore, great care is required to formulate a vaccine to contain a virus titer that is not only safely below the amount that leads to adverse events, but that also maintains sufficient efficacy in view of the virus titer loss due to lyophilization and subsequent storage.

Furthermore, there is a limitation to the size of a lyophilization vials and/or number of doses contained within such vials due to relatively small standard stopper sizes for the tops of these vials. Therefore, large volumes of liquid become difficult to sublimate through the relatively small openings. Therefore, there is a need for new live attenuated avian virus vaccines that can reliably retain their virus titers at a safe and efficacious level.

Additionally, the smallest vial size available for most poultry vaccines is 1000 doses. Vials of lyophilized vaccines must be used in their entirety after rehydration of the freeze dried cake. This makes it difficult for the growing number of small poultry farmers who have to buy a large dose size to vaccinate only a few birds. There is therefore a need for poultry vaccines where a single vial can be used over multiple days, weeks or even months, thus reducing the cost and encouraging vaccination of smaller flocks.

Finally, avian vaccines can be packaged with as many as 25,000 doses per vial, which are subsequently mixed by the user and placed in drinking water or sprayed on the flock. This requires the user to remove the metal sealing ring and stopper, flush the lyophilized vaccine out by submerging the vial in a large bucket of water, then mixing the solution with a large whisk or paddle. This is neither hygienic for the user or the poultry species for which the vaccine is intended. Indeed, dealing with lyophilized vials is particularly vexing in a commercial environment where the vaccine recipients, e.g., the fowl, reside.

The citation of any reference herein should not be construed as an admission that such reference is available as "prior art" to the instant application.

SUMMARY OF THE INVENTION

In order to overcome the deficiencies of current vaccines, the present invention provides novel liquid stable, live, poultry virus vaccines, as well as their corresponding immunogenic compositions. The liquid stable, live, poultry virus vaccines of the present invention can remain efficacious for extended periods such as 6, 7, 9 months or longer (e.g., about 1 to up to 3 years). The present invention also provides methods of administering such vaccines to an avian. The present invention further provides methods of preventing a disease in an animal, e.g., an avian, through administering a vaccine of the present invention.

Accordingly, the present invention provides liquid stable vaccines, including multivalent vaccines, that comprise a live virus. In certain embodiments the live virus is an attenuated virus. In other embodiments the live virus is a recombinant virus. In particular embodiments the live virus is both attenuated and recombinant. Recombinant viruses of the present invention can also encode a heterogeneous protein. In particular embodiments of this type, the heterogeneous protein is a virus or bacterial antigen.

In particular embodiments, the vaccine comprises a sugar additive that is a sugar alcohol and/or an amino acid. In certain embodiments the vaccine comprises 5 to 40% (w/v) of a sugar alcohol. In particular embodiments, the vaccine comprises 10 to 30% (w/v) of a sugar alcohol. In particular embodiments, the vaccine comprises 15 to 25% (w/v) of a sugar alcohol. In related embodiments the vaccine comprises 10 to 20% (w/v) of a sugar alcohol. In other embodiments, the vaccine comprises 20 to 25% (w/v) of a sugar alcohol. In still other embodiments, the vaccine comprises 25 to 40% (w/v) of a sugar alcohol. In more particular embodiments, the vaccine comprises 12 to 18% (w/v) of a sugar alcohol. In even more particular embodiments, the vaccine comprises about 15% (w/v) of a sugar alcohol. In related embodiments, the vaccine comprises about 23% (w/v) of a sugar alcohol. In certain embodiments, the liquid stable virus vaccines of the present invention comprise two or more sugar alcohols, with the total amount of the sugar alcohol in the liquid stable vaccines being 5-40% (w/v). In other such embodiments, the liquid stable virus vaccines of the present invention comprise two or more sugar alcohols, with the total amount of the sugar alcohol in the liquid stable vaccines being 25-40% (w/v).

In particular embodiments of the liquid stable virus vaccines of the present invention the sugar alcohol is sorbitol. In an alternative embodiment of this type, the sugar additive is mannitol. In related embodiments, the liquid stable vaccines further comprise a sugar additive that is a non-sugar alcohol, wherein the total amount of the sugar alcohol and the non-sugar alcohol in the liquid stable vaccine is 15-40% (w/v). In other embodiments, the liquid stable vaccines further comprise a sugar additive that is a non-sugar alcohol, wherein the total amount of the sugar alcohol and the non-sugar alcohol in the liquid stable vaccine is 25-40% (w/v). In particular embodiments, the non-sugar alcohol, sugar additive is trehalose. In still other embodiments, the non-sugar alcohol, sugar additive is dextrose. In yet other embodiments, the non-sugar alcohol, sugar additive is sucrose. In a particular embodiment of this type, the sugar additive is a combination of sucrose (non-sugar alcohol) and sorbitol (sugar alcohol). In a more particular embodiment of this type, the sugar additive is a combination of 10-25% sorbitol and 5-20% sucrose. In other embodiments of this type, the sugar additive is a combination of 15-30% sorbitol and 10-25% sucrose. In a still more particular embodiment of this type, the sugar additive is a combination of 15% sorbitol and 10% sucrose. In particular embodiments the non-sugar alcohol, sugar additive is actually a combination of two or more non-sugar alcohol, sugar additives.

The liquid stable vaccines of the present invention can range in pH from pH 6.0 to pH 8.0. In certain embodiments the pH range is from pH 6.5 to pH 7.8. In particular embodiments the pH range is from pH 6.8 to pH 7.5. In other particular embodiments the pH range is from pH 6.6 to pH 7.4. In more particular embodiments the pH range is from pH 7.0 to pH 7.4. In an even more particular embodiment the pH is 7.2.

The liquid stable vaccines of the present invention can comprise a buffer. In a particular embodiment of this type, the buffer comprises 2.5 to 50 mM phosphate, e.g., sodium phosphate (NaPHOS) or potassium phosphate (KPHOS). In a related embodiment, the buffer comprises 5 to 25 mM phosphate. In particular embodiments, the buffer comprises 10 to 20 mM phosphate.

In yet other embodiments the buffer (i.e., buffer solution) can further comprise 0.15 to 0.75 M arginine. In particular embodiments the buffer comprises 2.5 to 50 mM phosphate and 0.15 to 0.75 M arginine. In more particular embodiments the buffer comprises 5 to 25 mM phosphate and 0.15 to 0.75 M arginine. In still more particular embodiments the buffer comprises 10 to 20 mM phosphate and 0.3 to 0.5 M arginine. In other embodiments the buffer comprises 2.5 to 50 mM phosphate. In a related embodiment, the buffer comprises 5 to 25 mM Tris. In particular embodiments, the buffer comprises 10 to 20 mM Tris. In related embodiments the Tris buffer comprises histidine.

The liquid stable vaccines of the present invention can comprise an amino acid. In certain embodiments as detailed above, the amino acid is arginine. In other embodiments, the amino acid is methionine. In still other embodiments, the amino acid is glycine. In yet other embodiments, the amino acid is glutamic acid. In related embodiments, the liquid stable vaccines comprise both arginine and methionine. In other embodiments, the liquid stable vaccines comprise both arginine and glycine. In yet other embodiments, the liquid stable vaccines comprise both glycine and methionine. In related embodiments, the liquid stable vaccines comprise both glutamic acid and methionine. In other embodiments, the liquid stable vaccines comprise both glutamic acid and glycine. In yet other embodiments, the liquid stable vaccines comprise both glutamic acid and arginine.

In related embodiments, the liquid stable vaccines comprise arginine, glutamic acid, and methionine. In other embodiments, the liquid stable vaccines comprise arginine, glutamic acid, and glycine. In yet other embodiments, the liquid stable vaccines comprise arginine, glutamic acid, and methionine. In still other embodiments, the liquid stable vaccines comprise arginine, glycine, and methionine. In yet other embodiments, the liquid stable vaccines comprise arginine, glycine, and methionine. In particular embodiments, the liquid stable vaccines comprise arginine, glycine, methionine, and glutamic acid.

In particular embodiments the final concentration of arginine, or glutamic acid, or glycine in the liquid stable vaccine is 0.15 to 0.75 M. In related embodiments, the final concentration of arginine, or glutamic acid, or glycine in the liquid stable vaccine is 0.25 to 0.75 M. In more particular embodiments, the final concentration of arginine, or glutamic acid, or glycine in the liquid stable vaccine is 0.2 to 0.6 M. In more particular embodiments, the final concentration of arginine, or glutamic acid, or glycine in the liquid stable vaccine is 0.2 to 0.5 M. In still other embodiments, the final concentration of arginine, or glutamic acid, or glycine in the liquid stable vaccine is 0.25 to 0.45 M. In even more particular embodiments, the final concentration of arginine, or glutamic acid, or glycine in the liquid stable vaccine is about 0.45 M. In other particular embodiments, the final concentration of arginine, or glutamic acid, or glycine in the liquid stable vaccine is about 0.3 M.

In particular embodiments the final combined concentration of arginine together with glutamic acid and/or glycine in the liquid stable vaccine is 0.15 to 0.75 M. In related embodiments, the final concentration of arginine together with glutamic acid and/or glycine in the liquid stable vaccine is 0.25 to 0.75 M. In other embodiments, the final combined concentration of arginine together with glutamic acid and/or glycine in the liquid stable vaccine is 0.2 to 0.6 M. In more particular embodiments, the final combined concentration of arginine together with glutamic acid and/or glycine in the liquid stable vaccine is 0.3 to 0.5 M. In still other embodiments, the final concentration of arginine and glutamic acid, or glycine in the liquid stable vaccine is 0.25 to 0.45 M. In even more particular embodiments, the final combined concentration of arginine together with glutamic acid and/or glycine in the liquid stable vaccine is about 0.45 M. In other particular embodiments, the final concentration of arginine together with glutamic acid and/or glycine in the liquid stable vaccine is about 0.3 M.

In particular embodiments the final concentration of methionine in the liquid stable vaccine is 0.025 to 0.3 M. In related embodiments, the final concentration of methionine in the liquid stable vaccine is 0.04 to 0.15 M. In more particular embodiments, the final concentration of methionine in the liquid stable vaccine is 0.06 to 0.09 M. In even more particular embodiments, the final concentration of methionine in the liquid stable vaccine is about 0.07 M.

The liquid stable vaccines of the present invention also can comprise a stabilizer protein. The stabilizer protein can be an intact protein and/or a protein hydrolysate. In particular embodiments the stabilizer protein is gelatin. In more particular embodiments the stabilizer protein contained by the liquid stable vaccine of the present invention is 0.4 to 1.6% gelatin. In alternative embodiments the stabilizer protein is a hydrolysate of whole casein. In particular embodiments of this type the stabilizer protein contained by the liquid stable vaccine of the present invention is 0.5-2.0% of a hydro lysate of whole casein. In certain embodiments the hydrolysate of whole casein is a proteolytic hydrolysate of whole casein. In yet other embodiments, the stabilizer protein contained by the liquid stable vaccine of the present invention is lactoglobulin or a lactalbumin hydro lysate.

In addition, the liquid stable vaccines of the present invention can also further comprise a chelating agent. Such chelating agents can include, but are not limited to: ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS). The concentration of such chelating agents in the liquid vaccines of the present invention can vary from about 50 μM to 10 mM.

In particular embodiments the chelating agent is ethylenediaminetetraacetic acid (EDTA). In certain embodiments of this type the liquid stable vaccine comprises 0.050 to 1 mM EDTA. In particular embodiments the liquid stable vaccine comprises 0.25 to 0.75 mM EDTA. In more particular embodiments the liquid stable vaccine comprises about 0.5 mM EDTA.

In certain embodiments the liquid stable vaccines of the present invention can further comprise one or more free radical scavengers and/or antioxidants as a component. In a particular embodiment of this type a vaccine of the present invention comprises ascorbic acid. In a particular embodiment of this type the liquid stable vaccine comprises about 0.5 mM ascorbic acid. In a related embodiment the vaccine comprises alpha-tocopherol. In a particular embodiment of this type the liquid stable vaccine comprises about 0.5 mM alpha-tocopherol. In yet another embodiment, the vaccine comprises glutathione. In a particular embodiment of this type the liquid stable vaccine comprises about 3 mM glutathione. In still another embodiment, the vaccine comprises both alpha-tocopherol and ascorbic acid. In yet another embodiment the vaccine comprises both alpha-tocopherol and glutathione. In still another embodiment, the vaccine comprises both glutathione and ascorbic acid. In yet another embodiment the vaccine comprises ascorbic acid, alpha-tocopherol, and glutathione.

In related embodiments, the liquid stable vaccines of the present invention are maintained in sealed containers. In particular embodiments of this type, the liquid stable vaccines of the present invention are maintained in sealed containers that have an inert gas such as argon, nitrogen, or helium, above the liquid (e.g., have been back-filled with the inert gas).

The liquid stable vaccines of the present invention can further comprise an adjuvant. In particular embodiments of this type, the adjuvant is aluminum phosphate. In other such embodiments, the adjuvant is aluminum hydroxide. In still other embodiments, the adjuvant is a low molecular weight copolymer adjuvant which can form cross-linkage in solution to become a high molecular weight gel. In yet other embodiments, the adjuvant is made up of gel particles of sodium acrylate in water. In still other embodiments the adjuvant is a combination of two or more such adjuvants.

In particular embodiments the liquid stable vaccines of the present invention can further comprise a detergent and/or surfactant. In a certain embodiments of this type the surfactant is a polyoxyethylene-polyoxypropylene block copolymer. In a particular embodiment of this type the liquid stable vaccine comprises about 0.01% polyoxyethylene-polyoxypropylene block copolymer. In a specific embodiment of this type the polyoxyethylene-polyoxypropylene block copolymer is PLURONIC®F-68.

The liquid stable vaccines of the present invention can comprise a live attenuated poultry virus. In certain embodiments the live attenuated poultry virus is infectious bronchitis virus (IBV). In other embodiments the live attenuated poultry virus is infectious bursal disease virus (IBDV). In yet embodiments the live attenuated poultry virus is Newcastle disease virus (NDV). In still other embodiments the live attenuated poultry virus is Infectious Laryngotracheitis (ILTV). In yet other embodiments the live attenuated poultry virus is avian metapneumovirus (aMPV). In still other embodiments the live attenuated poultry virus is Mareks disease virus (MDV). In yet other embodiments the live poultry virus is Herpesvirus of Turkeys (HVT). [HVT is not pathogenic in chickens.]

The live poultry viruses can also be recombinant vectors. This is especially true for HVT and the two other MDVs, i.e., MDV1 and MDV2. Recombinant HVT vectors are already commercially available that encode antigens from Newcastle Disease Virus (e.g., the NDV "fusion" protein or otherwise referred to as the NDV F protein) or Infectious Laryngotracheitis virus (e.g., the ILTV gI and gD proteins). More recently, a unique recombinant HVT vector has been described that encodes antigens from both NDV (the NDV F protein) and ILTV (the ILTV gI and gD proteins) [see, U.S. Pat. No. 8,932,604, the contents of which are hereby incorporated by reference]. The liquid stable vaccines of the present invention can comprise any of these recombinant poultry virus vectors either individually or in any combination as described herein.

Accordingly, the liquid stable vaccines of the present invention can further comprise a killed virus and/or a killed bacterium (e.g., a bacterin) and/or a sub-fraction of a bacterin. Accordingly, any of the liquid stable vaccines of the present invention that comprise one or more live virus vaccines can further comprise a killed virus and/or killed bacterium and/or a sub-fraction of a bacterin, or even a parasite such as a live *Eimeria* that is either attenuated or non-attenuated.

In certain embodiments the liquid stable vaccine comprises a live attenuated IBV, a live attenuated IBDV, a live HVT, and a live attenuated MDV. In other embodiments the liquid stable vaccine comprises a live attenuated avian metapneumovirus, a live attenuated IBDV, a live attenuated NDV, and a live HVT. In still other embodiments, the liquid stable vaccine comprises a live attenuated IBV, a live attenuated IBDV, a live attenuated NDV, a live attenuated MDV, and a live attenuated aMPV. In yet other embodiments, the liquid stable vaccine comprises a live attenuated IBV, a live attenuated IBDV, a live attenuated NDV, a live attenuated MDV, a live aMPV, and a live attenuated Fowl Pox virus. In any of these embodiments, the live poultry virus can be a recombinant viral vector that encodes a heterologous antigen. In addition, any of the liquid stable vaccine of the present invention also can be combined with one or more attenuated or killed bacterial antigens such as *Pasteurella multocida, Salmonella enteritidis, Avibacterium paragallinarum, Clostridium perfringens* and *Mycoplasma gallisepticum* prior to administration. Examples of poultry vaccines (both monovalent and multivalent) that contain antigens and combinations of antigens that can be included in the liquid stable vaccines of the present invention can be found in Tables 1A-1C below.

The present invention further provides methods of aiding in the protection of an avian against a clinical disease that arises from an avian virus infection comprising administering a vaccine of the present invention to the animal. Accordingly, the present invention provides methods that comprise administering to a fowl any liquid stable vaccine of the present invention. In certain embodiments the administration is performed mucosally (by eye drop or drinking water). In other embodiments the administration is performed parenterally. In still other embodiments the administration is performed intradermally. In yet other embodiments the administration is performed transdermally.

In more specific embodiments, a vaccine of the present invention is administered to the animal by spray. In still other embodiments, the administration is performed by an in ovo route. In other specific embodiments, a vaccine of the present invention is administered to the avian intramuscularly. The present invention also includes the use of primary and/or booster vaccines.

In particular embodiments, the method comprises administering to the fowl a liquid stable vaccine of the present invention that comprises a live virus, e.g., a live attenuated virus. Accordingly, in specific embodiments methods of administering liquid stable vaccines of the present invention are provided that can comprise one or more live poultry virus selected from a live attenuated IBV, a live attenuated IBDV, a live HVT, a live attenuated MDV, a live attenuated avian metapneumovirus, and/or a live attenuated NDV. In any of these embodiments, the live poultry virus in the vaccine can be a recombinant viral vector that encodes a heterologous antigen. In addition, prior to, together with, or subsequent to the administering of any of the liquid stable vaccines of the present invention one or more attenuated or killed bacterial antigens such as *Pasteurella multocida, Salmonella enteritidis, Avibacterium paragallinarum, Clostridium perfringens* and *Mycoplasma gallisepticum* can also be administered.

Methods of making any and all of the liquid stable vaccines of the present invention are also provided. In certain embodiments the method comprises combining a therapeutically effective amount of a live attenuated virus with e.g., a 5-40% sugar additive, (e.g., a sugar alcohol or a combination of a sugar alcohol with a non-sugar alcohol), an amino acid, and a buffered solution at pH 6.0 to pH 8.0 to form a liquid stable vaccine. The amino acid can be arginine, glycine, glutamic acid, methionine, or combinations of arginine, glycine, glutamic acid and/or methionine. In particular embodiments the arginine and/or glycine and/or glutamic acid has a final concentration of 0.15 to 0.75 M in the liquid stable vaccine. In certain embodiments the vaccine further comprises methionine at a final concentration of 0.025 to 0.3 M in the liquid stable vaccine. In particular embodiments the therapeutically effective amount of a live attenuated virus is a therapeutically effective amount of a live attenuated avian virus. In specific embodiments of this type, the therapeutically effective amount of a live attenuated poultry virus includes therapeutically effective amounts of live attenuated IBV, live attenuated IBDV, live attenuated Newcastle disease virus, live attenuated Mareks disease virus, and live attenuated avian metapneumovirus. In a more particular embodiment of this type, the therapeutically effective amount of a live attenuated poultry virus includes therapeutically effective amounts of live attenuated IBV, live attenuated IBDV, live attenuated Newcastle disease virus, live attenuated Mareks disease virus, live attenuated avian metapneumovirus, and live attenuated fowl pox virus.

These and other aspects of the present invention will be better appreciated by reference to the following Detailed Description.

DETAILED DESCRIPTION OF THE INVENTION

Because the liquid stable poultry virus vaccines of the present invention comprise live viruses, e.g., live attenuated viruses, heretofore particular care would have been needed during the formulation of the vaccine to maintain the titer of the attenuated viruses at a level that is safely below that which can lead to a significant adverse event. Indeed, most live attenuated poultry virus vaccines are lyophilized, and lyophilization can lead to substantial declines in the efficacy of the attenuated live virus vaccines both due to the lyophilization process itself, as well as over time during long-term storage.

The present invention has overcome this problem by providing liquid stable poultry vaccines that remain efficacious, even during storage, without needing to increase the initial titer of the live attenuated viral antigen above a reliably safe level. As an additional benefit, the present invention provides a means for lowering the cost of manufacture of the vaccines provided by significantly reducing the amount of live attenuated poultry viruses necessary to make such a safe and efficacious vaccine. In addition, the live attenuated poultry virus vaccines of the present invention are more convenient to use than their lyophilized counterparts. Accordingly, the present invention provides safe and efficacious live attenuated poultry virus vaccines that can be stored as liquids at refrigerated temperatures and still remain stable for 5 to 7 months, 6 to 9 months, 9 to 12 months, 12 to 18 months, and/or 18 to 24 months and/or even longer. Unlike its lyophilized counterpart, the liquid stable vaccines of the present invention do not have to be used as soon as it is rehydrated, because they are always hydrated. Since poultry vaccines often come in 1000 dose vials as the smallest presentation, those with smaller farms will use only a fraction of the lyophilized vaccine that they purchased. With the liquid stable poultry vaccine, smaller farms can continue to use the same vaccine vial over several weeks or months, providing the vaccine is handled properly and not contaminated. This opens a whole new exclusive market to smaller farms.

Moreover surprisingly, the liquid stable live poultry virus vaccines of the present invention can include poultry viruses of any type. Thus, the liquid stable live virus vaccines of the present invention can include both enveloped and non-enveloped poultry viruses. In addition, the liquid stable live virus vaccines of the present invention can include live attenuated poultry viruses having single-stranded RNA genomes, single-stranded DNA genomes, or double-stranded DNA genomes.

The use of singular terms for convenience in the description is in no way intended to be so limiting. Thus, for example, reference to a "sugar additive" includes reference to one or more of such sugar additives, unless otherwise specified. The use of plural terms is also not intended to be limiting, unless otherwise specified. Similarly, a chemical compound that can be referred to as an acid or its corresponding base, unless otherwise specified, when denoted herein as either is intended to mean either form of the compound. Thus, the use of the term glutamic acid is meant to include glutamate and vice versa.

As used herein the term "poultry" can include chickens, turkeys, ducks, geese, quail, and pheasants.

As used herein the terms "avian" and "fowl" are used interchangeably with both terms intended to include poultry as defined above.

As used herein, a "vaccine" is a composition that is suitable for application to an animal (including, in certain embodiments, humans) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines.

As used herein, a "multivalent vaccine" is a vaccine that comprises two or more different antigens. In a particular embodiment of this type, the multivalent vaccine stimulates the immune system of the recipient against two or more different pathogens.

As used herein, a "liquid stable" vaccine is a vaccine maintained as a liquid (including a liquid multivalent vaccine) that remains efficacious for at least six months when stored at or below 7° C. (e.g., in a standard refrigerator, and/or at 0° C.-7° C.). In particular embodiments a liquid stable vaccine remains efficacious when stored at or below 7° C. for at least 9 months. In more particular embodiments a liquid stable vaccine remains efficacious when stored at or below 7° C. for at least 1 year. In even more particular embodiments a liquid stable vaccine remains efficacious when stored at or below 7° C. for at least 1.5 years. In still more particular embodiments a liquid stable vaccine remains efficacious when stored at or below 7° C. for at least 2.0 to 3 years.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The term "prophylactically-effective amount" refers to the amount of a composition that when administered to poultry significantly reduces the likelihood and/or extent of an infection/infestation due to a given pathogen.

"Metaphylaxis" is the timely mass medication of an entire group of animals to eliminate or minimize an expected outbreak of disease, e.g. in one or more animals at high risk of infection/infestation.

The term "chemoprophylaxis" refers to the administration of a medication/treatment, e.g., one or more prophylactic compositions, for the purpose of preventing or reducing viral, bacterial, and/or parasitic infection/infestation; and/or preventing or reducing disease and/or symptoms related to that infection/infestation.

The term "prophylactic composition" refers to any agent used singularly or in combination with other agents that significantly reduces the likelihood and/or extent of an infection/infestation due to a given pathogen in poultry. In one such embodiment the poultry are at high risk of developing poultry respiratory disease following commingling, changes in weather, changes in nutrition, and/or other stressors that can initiate a symptom and/or a disease related to the presence of the viral, bacterial, or parasitic pathogens commonly associated with poultry, targeted by the agent or combination of agents.

As used herein, the term "therapeutically effective amount" is an amount of a given antigen, e.g., a live attenuated poultry virus, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen. An "efficacious" vaccine retains sufficient titer for a given antigen to be compliant with the regulatory requirements for that antigen for the jurisdiction where the vaccine is administered, e.g., the administration of a vaccine in the United States is governed by the United States Department of Agriculture (USDA).

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous sugar, e.g., dextrose and/or glycerol, solutions can be employed as carriers, particularly for injectable solutions. In addition, the carrier can be and/or comprise a hydrocolloid and/or polymer solution e.g., to thicken the poultry vaccines that are to be sprayed on to the avian.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, "systemic administration" is administration into the circulatory system of the body (comprising the cardiovascular and lymphatic system), thus affecting the body as a whole rather than a specific locus such as the gastro-intestinal tract (via e.g., oral, spray on) and the respiratory system (via e.g., eye drop administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein, "in ovo" is administration into the egg which the avian is still growing inside of it. This type of administration can result in the vaccine being taken up orally by the avian while in the egg, or can be accidentally injected intramusculary, or can be absorbed through the yolk sac.

As used herein a "sugar additive" is a 5 to 12 carbon sugar (e.g., sucrose, maltose, trehalose, dextrose, lactose, glucose, fructose, galactose) or sugar alcohol/polyol (e.g., sorbitol, mannitol, arabitol, inositol, maltitol, glycerol). Unless otherwise specifically stated to the contrary, the percent (%) of the sugar additive is provided as a weight (w) of the sugar additive to the volume (v) of the vaccine, (w/v) in the vaccine.

As used herein a "non-reducing sugar" is a sugar additive which in basic aqueous medium does not generate any compounds containing an aldehyde group. Examples of non-reducing sugars of the present invention include sucrose and trehalose.

As used herein, the terms "non-sugar alcohol" and "non-alcohol sugar" are used interchangeably. A sugar additive that is a "non-sugar alcohol" (or "non-alcohol sugar") as used herein, can be any sugar additive that is not a sugar alcohol, e.g., a non-reducing sugar.

As used herein, unless otherwise specifically stated to the contrary, the percent (%) of a solid additive, e.g., sugar additive or gelatin, in a vaccine is based on a 1% solution being 1 g of solid/100 ml of vaccine volume (w/v).

As used herein, unless otherwise specifically stated to the contrary, the percent (%) of a liquid additive, e.g., ethanol, in a vaccine is based on a 1% solution being 1 ml of liquid additive/100 ml of vaccine volume (v/v).

As used herein, the term, "approximately," is used interchangeably with the term "about" and generally signifies that a value is within twenty-five percent of the indicated value, unless otherwise indicated, i.e., a concentration of "about" 2 mM EDTA can be 1.5 mM to 2.5 mM EDTA.

As used herein, unless otherwise specifically stated to the contrary, the pH value provided is the pH value determined/measured at 25° C.

Because the liquid stable vaccines of the present invention ideally range in pH from pH 6.0 to pH 8.0, the liquid stable vaccines of the present invention can comprise a buffer. Buffers for use in the liquid stable vaccines of the present invention include but are not limited to: potassium phosphate, sodium phosphate, Tris, Tris-Histidine, BIS-Tris, BIS-Tris-Propane, sodium or potassium pyrophosphate, imidazole, PIPES, ACES, MOPS, MOPSO, BES, TES, tricine, glycylglycine, and HEPES. The buffers can be brought to the desired pH with the use of any suitable counter ion.

The hydrolysate of whole casein that can be used in the liquid stable vaccines of the present invention can be obtained by a number of procedures including e.g., as an acid hydrolysate or an enzymatic hydrolysate. Such hydrolysates contain in the form of mixed amino acids and peptides having all of the amino acids originally present in casein. One pancreatic hydrolysate of whole casein that can be used in the liquid stable vaccines of the present invention is sold as CASEIN HYDROLYSATE ENZYMATIC® by MP Biomedicals. Comparable products are sold under the name of NZ-AMINE®, NZ-AMINE® A, NZ-AMINE® AS, and NZ-AMINE® B, and Tryptone by Sigma-Aldrich.

Examples of hydrocolloids that can be comprised by the vaccines of the present invention include: gelatin, starch polymers, and gums, such as xanthum gum, carragenin, and gum Arabic (acacia gum).

Multivalent Vaccines:

The present invention provides liquid stable multivalent vaccines. A liquid stable multivalent poultry vaccine of the present invention can include two or more antigens including one or more of the following live attenuated poultry viruses: IBV, IBDV, NDV, MDV, ILTV, aMPV, and/or a recombinant HVT encoding one or more heterologous antigens. As noted above, a liquid stable multivalent poultry vaccine of the present invention can also include one or more of the following live attenuated viruses: IBV, IBDV, NDV, ILTV, MDV, aMPV, and/or a recombinant HVT encoding one or more heterologous antigens, along with one or more killed poultry viruses.

In addition, a liquid stable vaccine of the present invention can be subsequently combined with one or more live attenuated or killed bacterial vaccine comprising an antigen such as *Pasteurella multocida, Salmonella enteritidis, Avibacterium paragallinararum, Clostridium perfringens* and *Mycoplasma gallisepticum* and/or non-attenuated or attenuated parasite such as *Eimeria*, prior to administration. Examples of monovalent and multivalent vaccines that can be used in the liquid stable vaccines of the present invention are provided in Tables 1A-1C below:

TABLE 1A

| Live Virus Vaccines | |
|---|---|
| Single | Combo |
| MDV-1 (CVI-988) | MDV-1 + HVT (serotype 3 MDV) |
| Recombinant HVT/NDV | HVT/NDV + SB1 (serotype 2 MDV) |
| Recombinant HVT/ILT | HVT/ILT + SB1 |
| Recombinant HVT/NDV/ILT | Recombinant HVT/NDV/ILT + IBV |
| ILT | |
| *Infectious Bursal Disease Virus*/Gumboro (IBDV) | Combining IBDV strains |
| (ST-12 strain, 89/03 strain, D-78 strain, A-51 strain) | IBDV + Reo ± NDV |
| *Chicken Anemia virus* (CAV) | |
| *Fowl Pox Virus* (FPV) | FPV + *Avian Encephalomeyelitis virus* (AE) ± CAV |
| *Reo Virus* | |
| *Pigeon Pox Virus* | |
| *Infectious Bronchitis Virus* (Mass, Conn, Ark, GA98, Del 072 strains) | IBV (Mass + Conn); IBV (Mass + Ark) |

TABLE 1A-continued

Live Virus Vaccines

| Single | Combo |
|---|---|
| *Newcastle Disease Virus* (NDV) (C2, B2 or LaSota strains) | NDV (C2) + IBV (Mass) ± IBV (Conn)<br>NDV (B1) + IBV (Mass) + IBV (Conn)<br>NDV (B1) + IBV (Mass) + IBV (Ark)<br>NDV (LaSota) + IBV (Mass) + IBV (Conn) |

TABLE 1B

Live Bacteria/Parasite

| Single | Combo |
|---|---|
| *Pasteurella Multocida* (M-9 strain, or CU strain)<br>*Mycoplasma gallisepticum*<br>*Bordetella avium*<br>Avian *Adenovirus*-type II | |
| | *Eimeria* (*acervulina*, *mivati*, *maxima*, and *tenella* strains)<br>*Eimeria* (*tenella*, *mivati*, *acervulina*, *maxima*, *brunetti*, and *necatrix*)<br>*Eimeria* (*dispersa*, *meleagrimitis*, *adenoeides*, and *gallipavonis*) |

TABLE 1C

Killed Vaccines

| Single | Combo |
|---|---|
| *Clostridium Perfringens* Type A toxoid<br>*Haemophilus paragallinarum* bacterin | |
| | IBV (Mass) + *Salmonella enteritidis* bacterin<br>IBDV + Reo + IBV (Mass) + NDV<br>IBDV (ST-12 + Del E + GLS + AL2 strains) + Reo |

Adjuvants:

The vaccines of the present invention can either contain an adjuvant or alternatively not contain an adjuvant, often depending on the antigen(s) that the vaccine contains. In particular embodiments, the adjuvant comprises an aluminum salt. The use of aluminum salts in conjunction with live viral vaccines has been described. In particular embodiments the aluminum salt is chosen from the group consisting of aluminum phosphate, aluminum potassium phosphate, and aluminum hydroxide. One aluminum phosphate adjuvant is REHYDROPHOS® (General Chemical, Parsippany, N.J.). Examples of aluminum hydroxide adjuvants include: REHYDROGEL®, REHYDROGEL® HPA, or REHYDROGEL® LV (General Chemical, Parsippany, N.J. Other well-known adjuvants include hydrocarbon oils, polymers, saponins and/or an adjuvant made up of gel particles of sodium acrylate in water, e.g., MONTANIDE™ PET GEL A™ (Seppic, Paris France). One low molecular weight copolymer adjuvant can form cross-linkage in solution to become a high molecular weight gel, e.g., POLYGEN™ (MVP Laboratories, Omaha). When added, the amount of adjuvant is usually between about 1% and 20% (v/v) in the vaccine. In particular embodiments the amount of adjuvant is between about 2% to 10% (v/v). In more particular embodiments the amount of adjuvant is between about 3% to 6% (v/v).

Vaccine Administration:

The liquid stable virus vaccines of the present invention may be administered by any conventional means, for example, by systemic administration, including by parenteral administration such as, without limitation, subcutaneous or intramuscular administration. The liquid stable virus vaccines of the present invention also may be administered by mucosal administration, such as by spray on, oral, in ovo, and/or ocular administration. Alternatively, the vaccines may be administered via a skin patch, in a delayed release implant, scarification, or topical administration. It is contemplated that a liquid stable virus vaccine of the present invention also may be administered via the drinking water and/or food of the recipient poultry.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

In certain embodiments of the methods of the present invention, a virus vaccine of the present invention that is suitable for mucosal administration comprises one or more of the following: a live attenuated IBV, a live attenuated IBDV, a live attenuated MDV, a live attenuated ILTV, a live attenuated aMPV, a live recombinant HVT virus, and a live attenuated NDV. In more particular embodiments the virus vaccine of the present invention that is suitable for mucosal administration further comprises a live attenuated IBV and one or more of the following: a live attenuated IBDV, a live attenuated MDV, a live attenuated ILTV, a live attenuated aMPV, a live recombinant HVT virus, and a live attenuated NDV.

The immunogenicity level may be determined experimentally by vaccine dose titration and challenge study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the species or breed (e.g., of an avian), age, weight, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.01 mL (eye drop applications) and 2.0 mL. A typical range for the administration volume is between 0.03 and 1.0 mL, and about 0.1 to 0.5 mL for intramuscular administration.

Included in the decision regarding the number of times a given vaccine is administered to an avian subject will be whether the avian subject is being raised for meat, for producing eggs, or as a pet. Accordingly, it is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose.

In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

The vaccines of the present invention can also contain an anti-bacterial such as an antibiotic. Examples of such antibiotics can include: 10-1000 µg/mL gentamicin, 0.5-5.0 µg/mL amphotericin B, 10-100 µg/mL tetracycline, 10-100 units/mL nystatin (mycostatin), 10-100 units/mL penicillin, 10-100 µg streptomycin, 10-100 µg polymyxin B, and 10-100 µg neomycin.

The present invention may be better understood by reference to the following non-limiting Example, which is provided as exemplary of the invention. The following Example is presented in order to more fully illustrate embodiments of the invention. It should in no way be construed, however, as limiting the broad scope of the invention.

EXAMPLE

Stability of Liquid Poultry Virus Vaccines

Materials and Methods

Bulk antigen preparation: Frozen bulk IBV virus antigen was obtained from production and kept at <−60° C. until the time to blend the vaccine. The IBV bulk antigen has a titer around 9.1 $\log_{10}(EID_{50})$.

Materials:

Cell culture or higher grade sucrose and sorbitol are purchased from Fisher Scientific. Molecular biology grade L-arginine monohydrochloride with purity higher than 98% are purchased from Sigma. NZ Amine (bloom 250) solutions are prepared from the best available commercial reagents. The following solutions have been prepared and sterilized by autoclaving or 0.2 um filtration: 80% (w/v) sucrose, 70% (w/v) sorbitol, 1.2 M L-arginine monohydrochloride, 1.0 M potassium phosphate buffer (pH 7.2), tryptose phosphate broth (TPB) solution and 250 mg/mL gentamicin.

Stabilizer Solution and Vaccine Blend pH Adjustment:

The pH of the final vaccine blend can be critical to the stability of the virus in liquid. The pH is measured using a very sensitive pH probe and meter. The meter displays the pH to 3 significant figures to the right of the decimal. There is a separate temperature probe with meter and both must be in the solution and stable. This pH meter is capable of a 5 point calibration curve with 3 points being an absolute minimum. During the vaccine blend preparation, the pH of the stabilizer solution is adjusted to the target pH prior to adding the virus antigen, and the pH is measured again after mixing the stabilizer solutions and virus antigens.

Preparation of the Stabilizer Solutions:

Once the initial pH adjustment has been made, all formulations were filter sterilized using a 0.2 µM filter (PES is preferred filter matrix simply due to improved filter capacity). Currently filtration is performed using vacuum. A secondary benefit of vacuum filtering is the additional de-gassing of the formulation. After the formulation has been filter sterilized, it is sparged with argon gas to increase the depletion of $O_2$ which will hopefully yield lower reactivity of the formulation over time. Once the sparging is complete an argon overlay is placed prior to storage and a tight a seal is made. After the formulation is prepared, the pH is confirmed/adjusted to pH 7.2 at the desired temperature (e.g., 4°, 15°, or 25° C.), i.e., for many experiments performed herein the desired temperature was 4° C. If the formulation and previous procedures have been performed correctly the pH should be close to target pH. With an overnight incubation the pH may drift slightly due to the completion of chemical reactions associated with the earlier pH adjustment and further de-gassing.

Thawing Virus Bulk Antigen:

The frozen antigens are slowly thawed at room temperature (15-30° C.) or at refrigerated temperature (2-8° C.). The thawed antigen should be kept at 2-8° C. for no more than 8 hours prior to usage.

Preparation of Vaccine Blend:

To make a 200 mL of vaccine blend, each stock solution at indicated volume as listed in Table 3 was added to a sterilized container first, and the stabilizers and excipients were mixed using a stirring bar. After the stabilizer solutions and all excipients were thoroughly mixed, the virus antigens at the indicated volume were added into the container and thoroughly mixed. The generating of bubbles and foams were avoided during this mixing step. When the virus is added in a very short time frame (a few minutes) then the virus may be added with no further issues. When the virus is not immediately added, an argon overlay is put in place to displace residual $O_2$. Once the virus has been added a fresh argon overlay is put into place prior to mixing. The argon gas is added to the bottle using a low flow rate. After the vaccine blending is complete, the vaccine blend is kept at 2-8° C. until dispensing into small aliquots.

Filling the Vaccines:

The vaccine blend was dispensed into glass ampule vials at 1.8 mL per vial. Each vial is then back-filled and overlaid with argon gas. The ampule vials were flame sealed, labelled and then transferred into boxes, and stored in the incubator at the designated temperature.

Stability Testing at Elevated Temperature and Real-Time Conditions:

Liquid IBV vaccines in ampule vials were stored at 15° C. and 4° C. respectively in the corresponding incubators. At the designated time point, 2 or more vials from each formulation were retrieved and the titer of each antigen was measured by egg based titration assay and reported as an average egg infective dose ($EID_{50}$).

Analytical Methods

All embryo infective dose assays are performed in a clean cell environment. Manipulations and dilutions are done in a Class II biological safety cabinet under aseptic conditions. Eggs are surface disinfected prior to any manipulation, and all bottles, pipets, pipette tips and dilution tubes must be sterilized before use. All media and associated ingredients must be sterile.

IBV DE-072 Potency Assay:

The preferred method for determining potency of a given of infectious bronchitis virus stock is to assay for infectivity in embryonated, specific-pathogen-free chicken eggs. The geometric mean titer (GMT) of a virus stock is determined by inoculating 9 to 11 day old embryos, in the allantoic cavity with 0.1 ml viral fluids, diluted in tryptose phosphate broth (TPB) containing 29 µg/mL gentamycin. Between four and six dilutions (not to exceed tenfold) shall be used per test, and a minimum of five embryos should be inoculated per dilution. Eggs are incubated at 38-39° C. and with a relative humidity of 60-70% for seven days and candled daily. Deaths occurring during the first 24 hours shall be disregarded, but mortality between days 2 and 7 post inoculation are considered to be virus-specific. At least four viable embyros in each dilution shall survive beyond 24 hours of a valid test. After 7 days incubation, embryos are examined for evidence of typical IBV infection, such as stunting, curling, clubbing of the down or urate deposits in the mesonephros of the kidney. For comparative purposes, a minimum of six eggs are inoculated with TPB diluent to serve as negative controls, and a prepared reference of IBV DE-072 with known titer is assayed and used as a positive control. A satisfactory titration shall have at least one dilution with between 50 and 100 percent positives and at least one dilution with between 50 and 0 percent positives. The mean embryo infective dose ($EID_{50}$) can be calculated using either the Reed and Muench, or Spearman-Kärber method. For more accuracy, it is recommended that at least 3 replicate titrations are performed per sample stock tested and an average GMT determined.

Results and Conclusions

Several potential liquid stable formulations of IBV are shown in Table 2. These formulations were used to evaluate the contribution of different stabilizers and excipient for IBV stability in liquid. Stabl #17 is a formulation for a commericial product that is sold frozen at <-50° C. due to low stability. Stabl #17 contains 3.3% (w/v) NZ Amine and 3.3% (w/v) sucrose as stabilizers. Formulations P-01, P-02 and P-03 are three formulations containing a sugar additive (sorbitol and sucrose) and L-arginine as stabilizers. Table 2 shows the final concentration of each stabilizer or excipient in final vaccine blend for each formulation. All formulations use 10 mM KPO4 as a buffer to provide a pH value around 7.2 and all four formulations contain 1.0 mg/mL gentamicin as a preservative. The target pH for the formulations is 7.2 and the actual pH after blending with IBV antigens is around pH 6.8 to 7.2. Formulation P-01 contains 15% (w/v) sorbitol and 0.3 M L-arginine as stabilizer. Formulation P-02 contains 15% (w/v) sorbitol and 0.45 M L-arginine as stabilizer. Formulation P-03 contains 15% (w/v) sorbitol, 10% (w/v) sucrose and 0.3 M L-arginine as stabilizer. TPB is used as filler solution for adjusting to the final target volume.

Batches of 200 mL of experimental vaccine were prepared by combining stabilizers, excipients, and preservatives together from stock solutions into a sterile bottle in a clean hood. For Stabl #17, 67 mL of 3× stabilizer #17 [10% sucrose (w/v) and 10% NZ Amine (w/v)], were thoroughly mixed with 65.2 mL TPB solution and 0.8 mL 100-250 mg/mL gentamicin solution. For formulations P-01, P-02 and P-03, each stabilizer (sucrose, sorbitol, L-arginine), excipient (KPO4, TPB) were dispensed with preservatives (gentamicin), at the designated volumes indicated in Table 3. After the stabilizers, excipients and preservatives are thoroughly mixed; 67 mL of thawed IBV antigens was added to each formulation and thoroughly mixed. Each vaccine blend was then aliquoted into glass ampule vials at 1.8 mL/vial. The vaccine vials were backfilled with argon, flame sealed, and then put on stability testing at either 15° C. or 4° C.

At designated time points after incubation at 15° C. and 4° C., a minimum of two vials from each formulation were retrieved from the incubator, and the titer of IBV were determined using $EID_{50}$ based potency assay. Table 4 and 5 show the average titer of IBV samples in each formulation after storage for up to 17 weeks at 15° C. and up to 12 months at 4° C. respectively. As shown in Table 4, IBV virus titer drops 2.8 log from day 0 to week 4.5 in formulation Stabl #17 during storage at 15° C. In marked contrast, IBV in the other three formulations (P-01, P-02 and P-03) are all stable relative to day 0 when stored at 15° C. The titer changes in all three formulations at 15° C. at week 1, 2, and 4.5 weeks relative to time 0 are all within the potency assay variation (0.5 log). The data in Table 4 confirm that IBV is not stable in the current product formulations, e.g., Stabl #17, but are stable in the formulations P-01, P-02 and P-03 up to 4.5 weeks at 15° C.

In addition, real time stability data at 4° C. also were collected [Table 5]. As seen with the 15° C. stability data, at 4° C. IBV in Stabl #17 showed a significant loss of titer by the first time point (3 months), and was essentially inactive by the second time point (i.e., at 6 months) whereas all three formulations, i.e., P-01, P-02, and P-03 provided significantly improved stability. The 4° C. stability data indicates that P-01, P-02 and P-03 provide improved IBV stability than current formulation Stabl #17, and that formulation P-03 is the best candidate among the three, showing essentially no titer change compared to day 0 up until 7 months storage at 4° C.

Based on the 15° C. stability data in Table 4, the stability of IBV in each formulation is analyzed using first order polynomial regression. Using the equation generated from the regression analysis, the time required for 1.0 log titer drop at 15° C. is calculated and listed at the bottom row of Table 6. The time required for 1.0 log titer drop for IBV is 1.6, 16.6, 22.7 and 49.8 weeks in formulation Stabl #17, P-01, P-02 and P-03, respectively. This analysis indicates that stabilizers in formulation P-01, P-02 and P-03 make different contributions. Comparison of formulation P-01 and P-02 indicates that raising the concentration of L-arginine from 0.3 M to 0.45 M does not significantly improve the IBV stability. Comparison of formulations P-01 and P-03 indicates that the additional 10% sucrose did make significant improvement for the IBV stability. The significant stabilizing effects of the P-01, P-02, and P-03 formulations over Stabl #17 indicates that the combination of sorbitol, sucrose and L-arginine can be beneficial for the IBV stability in a liquid formulation. The IBV real time stability data at 4° C. in Table 5 is consistent with the projected relative stability generated from 15° C. stability data, and further confirms that all three new formulations, i.e., P-01, P-02 and P-03, perform significantly better than Stabl #17. Further, the P-03 formulation provides the best stability at a standard refrigerator temperature.

TABLE 2

Formulations of the Liquid IBV Vaccines

Final concentration of stabilizer and excipient and the final pH of vaccine blend

| Formltn. | NZ Amine (w/v) | Sorbitol (w/v) | Sucrose (w/v) | Arginine (M) | KPO4 (mM) | Target pH | Actual pH |
|---|---|---|---|---|---|---|---|
| Stabl #17 | 3.3% |  | 3.3% |  | 10 mM | 7.2 | 7.2 |
| P-01 |  | 15% |  | 0.3M | 10 mM | 7.2 | 6.9 |
| P-02 |  | 15% |  | 0.45M | 10 mM | 7.2 | 6.8 |
| P-03 |  | 15% | 10% | 0.3M | 10 mM | 7.2 | 6.9 |

Note:
The concentration listed for each formulation (Formltn.) is the final concentration in the vaccine blend.
KPO4 is potassium phosphate solution containing monobasic and dibasic potassium phosphate in a volume ratio that yields a pH of 7.2.
For NZ Amine, sorbitol, and sucrose, the concentration unit is weight by volume (w/v); For arginine and KPO4, the concentration unit is molar and millimolar, respectively.
All formulations also contain 1 mg/mL of gentamycin in the final vaccine blend.

TABLE 3

Liquid IBV Blending per 200 mL Vaccine

| Formltn. | Virus (3x) | TPB (1x) | Sorbitol (70% w/v) | Sucrose (80% w/v) | L-Arg (1.2M) | Gentamicin (250 mg/mL) | KPO4 (1.0M) |
|---|---|---|---|---|---|---|---|
| P-01 | 67 mL | 37.2 mL | 43 mL | 0 | 50 mL | 0.8 mL | 2 mL |
| P-02 | 67 mL | 12.2 mL | 43 mL | 0 | 75 mL | 0.8 mL | 2 mL |
| P-03 | 67 mL | 12.2 mL | 43 mL | 25 mL | 50 mL | 0.8 mL | 2 mL |

Note:
To prepare formulation Stabl #17, 67 mL Stabilizer #17 (containing 10% NZ Amine and 10% Sucrose) is blended with 65.2 mL TPB, 0.8 mL gentamicin (250 mg/mL) and 67 mL IBV bulk virus.
For all vaccine blends, the stabilizers (sorbitol, sucrose, L-Arg), excipients (TPB, KPO4) and preservative (gentamicin) were blended first before the virus was added to the formulation.

TABLE 4

Stability of IBV Vaccine During Storage at 15° C. in Different Formulations

| Storage Temperature | Incubation Time | Virus Titer $Log_{10}(EID_{50})$/mL | | | |
|---|---|---|---|---|---|
| | | Stabl #17 | P-01 | P-02 | P-03 |
| n/a | Day 0 | 7.5 | 7.4 | 7.2 | 7.0 |
| 15° C. | 1 week | 6.9 | 7.0 | 6.4 | 6.3 |
| 15° C. | 2 weeks | 6.3 | 6.8 | 7.1 | 7.0 |
| 15° C. | 4.5 weeks | 4.7 | 7.1 | 6.8 | 6.7 |
| 15° C. | 17 weeks | <2.0 | 5.4 | 6.2 | 5.5 |

Note:
The titer of the vaccine at each time point is the average of a minimum of 2 vials of samples from each formulation.
An IBV virus positive control is always included in each virus titration and is used to validate the virus potency assay at each time point.
The variation of this $EID_{50}$ based virus potency assay is 0.5 log or smaller.

TABLE 5

Stability of IBV Vaccine During Storage at 4° C. in Different Formulations

| Storage Temperature | Incubation Time | Virus Titer Log$_{10}$(EID$_{50}$)/mL | | | |
|---|---|---|---|---|---|
| | | Stabl #17 | P-01 | P-02 | P-03 |
| n/a | Day 0 | 7.5 | 7.4 | 7.2 | 7.0 |
| 4° C. | 3 months | 4.9 | 6.4 | 6.2 | 7.3 |
| 4° C. | 6 months | <2.0* | 5.3 | 6.0 | 6.9 |
| 4° C. | 7 months | — | — | — | 6.7 |
| 4° C. | 9 months | — | 4.9 | 4.6 | 5.6 |
| 4° C. | 12 months | — | 4.7 | 4.4 | 5.3 |

Note:
The titer of the vaccine at each time point is the average of a minimum of 2 vials of samples from each formulation, (except the * indicates that only a single vial was used for the specific measurement of Stabl #17).
An IBV virus positive control is always included in each virus titration and is used to validate the virus potency assay at each time point.

TABLE 6

IBV Stability Prediction and Projected Time for 1.0 Log Titer Loss at 15° C.

| | Stabl #17 | P-01 | P-02 | P-03 | |
|---|---|---|---|---|---|
| IBV stability slope | −0.6235 | −0.04581 | −0.0324 | −0.01564 | Log$_{10}$(EID$_{50}$)/week |
| Y-intercept when X = 0.0 | 7.519 | 7.161 | 6.936 | 6.779 | Log$_{10}$(EID$_{50}$) |
| Titer at time 0 | 7.5 | 7.4 | 7.2 | 7.0 | Log$_{10}$(EID$_{50}$) |
| Time for 1.0 log titer drop from Time 0 | 1.6 | 16.6 | 22.7 | 49.8 | Weeks |

Note:
Stability data in Table 4 were used to predict the IBV stability in different formulations.
Nonlinear first order polynomial regression is used to generate the prediction from data in Table 4, with IBV titer as the y value and storage time (weeks) as the x value.
The IBV stability slope is the titer change [Log$_{10}$(EID$_{50}$)] per week and the Y-intercept is the titer at time 0 based on the regression equation.
Based on the regression equation (IBV titer change vs. storage time), the projected time required for 1.0 log titer drop from time 0 is calculated for each formulation and listed at the bottom row of the table.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

We claim:

1. A liquid stable vaccine that comprises a live Infectious Bronchitis Virus (IBV), a 10-30% (w/v) sugar alcohol, and 0.2 to 0.6 M of an amino acid selected from the group consisting of arginine, glutamic acid, and glycine; wherein the liquid stable vaccine has a pH of 6.0 to 8.0.

2. The liquid stable vaccine of claim 1 wherein the sugar alcohol is sorbitol.

3. The liquid stable vaccine of claim 2 wherein the amino acid is arginine.

4. The liquid stable vaccine of claim 3, which further comprises a live poultry virus selected from the group consisting of an Infectious Bursal Disease Virus (IBDV), a Newcastle Disease Virus (NDV), a Marek's disease virus (MDV), an avian metapneumovirus (aMPV), a Herpesvirus of Turkey (HVT), and any combination thereof.

5. The liquid stable vaccine of claim 4 that further comprises a killed poultry virus.

6. The liquid stable vaccine of claim 4 that further comprises a bacterium selected from the group consisting of a live attenuated *Pasteurella multocida*, a live attenuated *Salmonella enteritidis*, a live attenuated *Avibacterium paragallinarum*, a live attenuated *Mycoplasma gallisepticum*, a live *Clostridium perfringens*, a killed *Pasteurella multocida*, a killed *Salmonella enteritidis*, a killed *Avibacterium paragallinarum*, a killed *Mycoplasma gallisepticum*, an inactivated toxoid of *Clostridium perfringens*, and any combination thereof.

7. The liquid stable vaccine of claim 1 further comprising a sugar additive that is a non-alcohol sugar, wherein the total amount of the sugar alcohol and the non-alcohol sugar in the liquid stable vaccine is 15-40% (w/v).

8. The liquid stable vaccine of claim 7 wherein the non-alcohol sugar is selected from the group consisting of sucrose and trehalose.

9. The liquid stable vaccine of claim 1 that further comprises a buffer.

10. The liquid stable vaccine of claim 1, wherein the IBV is selected from the group consisting of Delaware strain, Mass strain, Arkansas strain, Connecticut strain, Georgia strain, and any combination thereof.

11. The liquid stable vaccine of claim 1 that further comprises a live attenuated IBDV.

12. The liquid stable vaccine of claim 11 that further comprises a live attenuated NDV.

13. The liquid stable vaccine of claim 12 that further comprises a live attenuated MDV or a recombinant attenuated MDV vector that encodes a heterologous antigen.

14. The liquid stable vaccine of claim 1 that further comprises a live HVT, or a recombinant HVT vector that encodes a heterologous antigen.

15. The liquid stable vaccine of claim 14 that further comprises a live attenuated aMPV.

16. A method of vaccinating an avian against IBV comprising administering to the avian the liquid stable vaccine of claim 1.

17. The method of claim 16, wherein said administering is performed by subcutaneous injection.

18. The method of claim 16, wherein said administering is performed by spray or feeding.

19. A liquid stable vaccine that comprises a live Infectious Bronchitis Virus (IBV), at least 15% (w/v) sorbitol, and 0.25 to 0.45 M arginine; wherein the liquid stable vaccine has a pH of 6.0 to 8.0.

20. The liquid stable vaccine of claim 19, that comprises 15-40% (w/v) sorbitol.

21. The liquid stable vaccine of claim 20, that further comprises 5-20% (w/v) sucrose.

22. The liquid stable vaccine of claim 20, that comprises 15% (w/v) sorbitol, and 0.25 to 0.45 M arginine; wherein the liquid stable vaccine has a pH of 6.0 to 8.0.

23. A method of making a liquid stable vaccine against IBV that comprises combining a therapeutically effective amount of a live attenuated IBV with a 10-30% (w/v) sugar alcohol, and 0.2 to 0.60 M arginine; wherein the liquid stable vaccine has a pH of 6.0 to 8.0.

* * * * *